US012778864B2

(12) United States Patent
Rastrelli et al.

(10) Patent No.: US 12,778,864 B2
(45) Date of Patent: Nov. 3, 2026

(54) FUNCTIONALIZED BIOMIMETIC HYDROXYAPATITE

(71) Applicant: KALICHEM S.R.L., Rezzato (IT)

(72) Inventors: Gianbattista Rastrelli, Rezzato (IT); Francesco Rastrelli, Rezzato (IT)

(73) Assignee: KALICHEM S.R.L., Rezzato (IT)

( * ) Notice: Subject to any disclaimer, the term of this patent is extended or adjusted under 35 U.S.C. 154(b) by 268 days.

(21) Appl. No.: 18/559,605

(22) PCT Filed: May 4, 2022

(86) PCT No.: PCT/EP2022/062069
§ 371 (c)(1),
(2) Date: Nov. 8, 2023

(87) PCT Pub. No.: WO2022/233986
PCT Pub. Date: Nov. 10, 2022

(65) Prior Publication Data
US 2024/0299263 A1 Sep. 12, 2024

(30) Foreign Application Priority Data
May 5, 2021 (IT) ........................ 102021000011492

(51) Int. Cl.
*A61K 8/27* (2006.01)
*A61K 8/49* (2006.01)
*A61Q 11/00* (2006.01)
*A61Q 17/00* (2006.01)

(52) U.S. Cl.
CPC .............. *A61K 8/27* (2013.01); *A61K 8/4926* (2013.01); *A61Q 11/00* (2013.01); *A61Q 17/005* (2013.01)

(58) Field of Classification Search
CPC ...... A61Q 17/005; A61Q 11/00; A61Q 19/00; A01N 55/02; A01N 59/04; A01N 33/12; A01N 59/06; A01N 47/44; A01N 43/16; A61K 8/4926; A61K 8/43; A61K 8/27; A61K 8/24; A61K 8/416; A61K 2800/524; A61K 2800/10
See application file for complete search history.

(56) References Cited

U.S. PATENT DOCUMENTS 8,367,043 B2 * 2/2013 Gazzaniga ............... A61K 8/24
977/773

FOREIGN PATENT DOCUMENTS

| | | | | |
|---|---|---|---|---|
| EP | 0539651 | | 5/1993 | |
| JP | 5973585 | B2 * | 8/2016 | ............ C01B 25/16 |
| KR | 20040081936 | | 9/2004 | |
| KR | 20080101954 | A | 11/2008 | |
| WO | 2013068020 | A1 | 5/2013 | |
| WO | 2018010962 | | 1/2018 | |
| WO | 2022233986 | A1 | 11/2022 | |

OTHER PUBLICATIONS

Mohammad et al., Controlling the pore characteristics of mesoporous apatite materials: Hydroxyapatite and carbonate apatite, Ceramics International 41 (2015) 10624-10633 (Year: 2015).*
Okada et al., Adsorption and desorption behaviors of cetylpyridinium chloride on hydroxyapatite nanoparticles with different morphologies, Dent Mater J. 2016;35(4):651-8. 2015-420. (Year: 2016).*
ISR-WO dated Aug. 18, 2022 for parent application PCT/EP2022/062069.
Stigter M et al, "Incorporation of different antibiotics into carbonated hydroxyapatite coatings on titanium implants, release and antibiotic efficacy", Journal of Controlled Release, Elsevier, Amsterdam, NL, vol. 99, No. 1, Sep. 14, 2004 (Sep. 14, 2004), p. 127-137.
Ayuda Nur Sukmawati et al., "Carbonated Hydroxyapatite Containing Propolis as an Antibacterial Agent Candidate against Aggregatibacter actinomycetemcomitans | Sukmawati | Majalah Obat Tradisional", Dec. 23, 2020 (Dec. 23, 2020), p. 196-200.
Carlos a Soriano de Souza et al., "Adsorption of chlorhexidine on synthetic hydroxyapatite and in vitro biological activity", May 18, 2011 (May 18, 2011), vol. 87, No. 2, p. 310-318.

* cited by examiner

*Primary Examiner* — Lezah Roberts
(74) *Attorney, Agent, or Firm* — Vorys, Sater, Seymour and Pease LLP

(57) ABSTRACT

The present invention relates to a carbonate-hydroxyapatite functionalized with a germicide, chosen among chlorhexidine and its salts, benzalkonium halides, diisobutyl phenoxyethoxyethyl dimethyl benzyl ammonium halides, alkyl dimethyl ethylbenzyl ammonium halides, cetylpyridinium halides and mixtures thereof.
The present invention also relates to cosmetic compositions, such as oral care compositions or skin-care compositions, comprising said functionalized carbonate-hydroxyapatite.

14 Claims, 3 Drawing Sheets

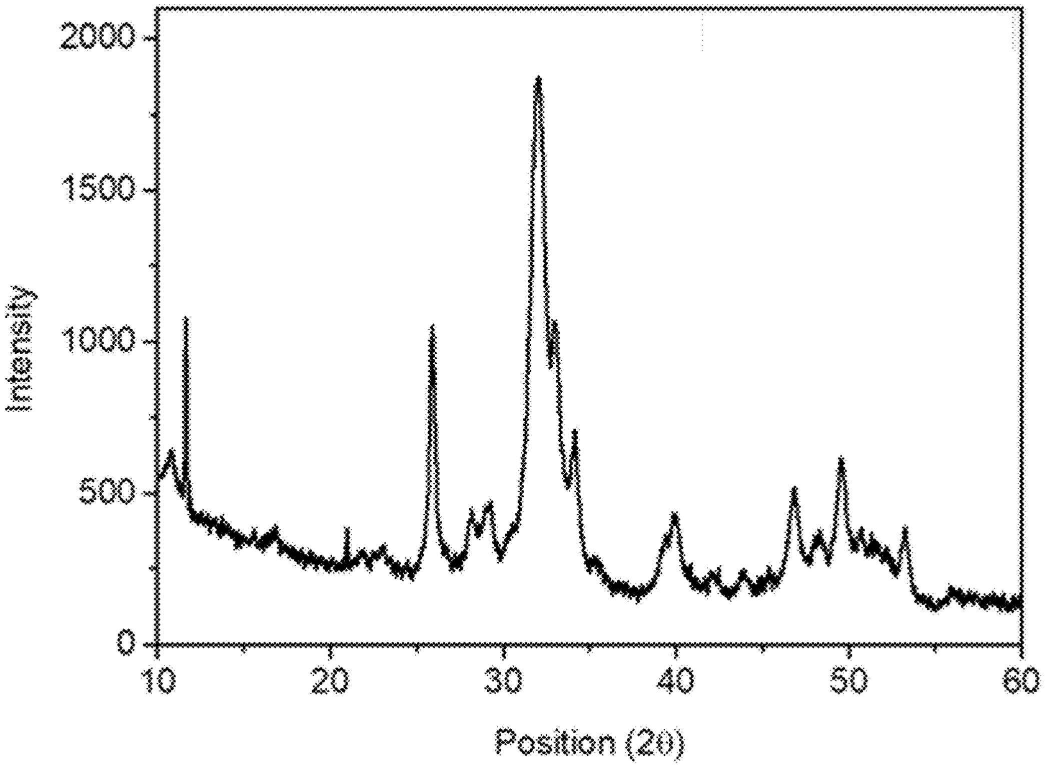
Figure 1. X-ray diffraction spectrum of the functionalized C-HAP of Example 1.

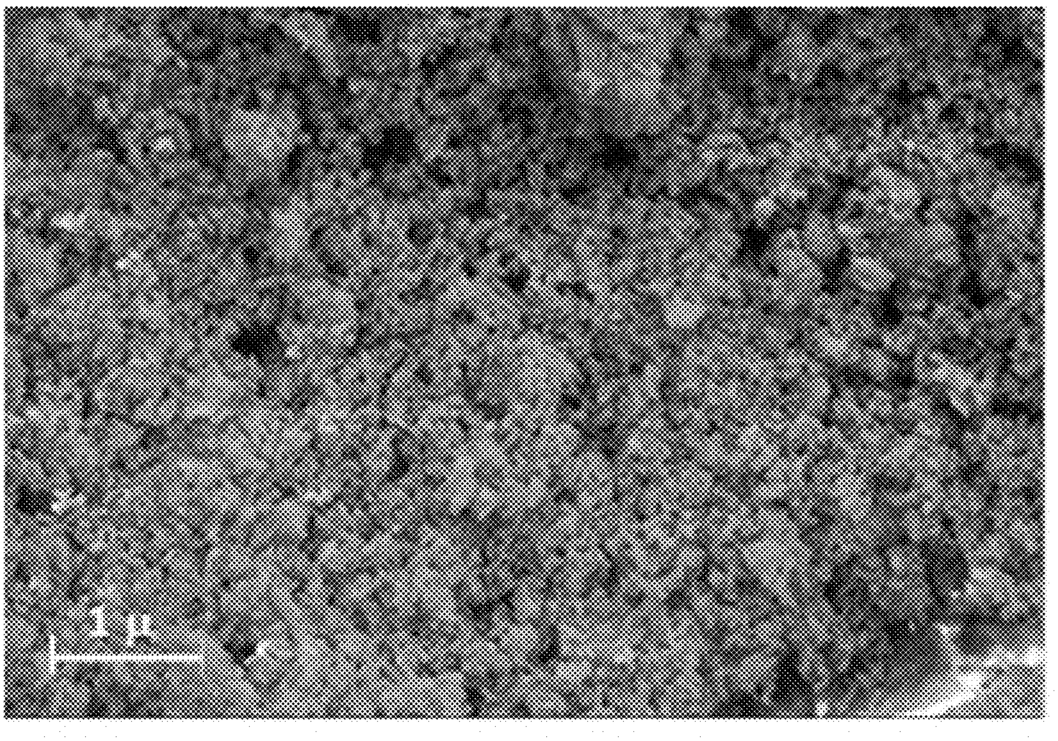
Figure 2. SEM image of a C-Hap.

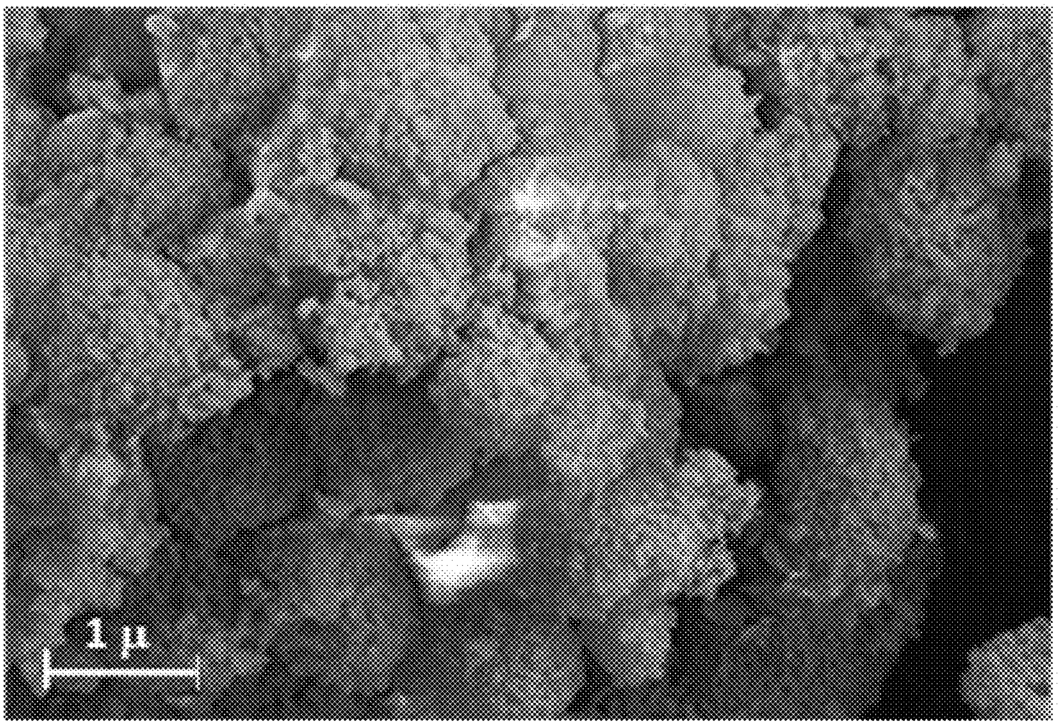
Figure 3. SEM image of the functionalized C-Hap of Example 1.

FUNCTIONALIZED BIOMIMETIC HYDROXYAPATITE

TECHNICAL FIELD

The present invention relates to a carbonate-hydroxyapatite functionalized with a germicide, chosen among chlorhexidine and its salts, benzalkonium halides, diisobutyl phenoxyethoxyethyl dimethyl benzyl ammonium halides, alkyl dimethyl ethylbenzyl ammonium halides, cetylpyridinium halides and mixtures thereof.

The present invention also relates to cosmetic compositions, such as oral care compositions or skin-care compositions, comprising said functionalized carbonate-hydroxyapatite.

BACKGROUND ART

Hydroxyapatite, $Ca_{10}(PO_4)_6(OH)_2$, is a compound present in the human body, being the main mineral constituent of bone tissue and of enamels. Indeed, 99% of the calcium in the human body is stored in bone tissue in the form of hydroxyapatite. Because of its excellent biocompatibility, synthetic hydroxyapatite is used for artificial bones, artificial tooth roots, bone fillers, pharmaceutical carriers and the like. In more recent years, synthetic hydroxyapatite has also been applied to cosmetics, such as toothpastes, sunscreens, and the like.

In oral care, for example, hydroxyapatite is currently used as a remineralizer material in toothpastes, chewing gum and in tooth whitening post-treatments; as a filler material in compound polymeric materials in the preparation of dental pieces; providing a long lasting remineralisation of the teeth.

In recent times, hydroxyapatite has been proposed as carrier for antimicrobial agents, such as metal ions or quaternary ammonium salts and other germicidal actives.

EP 0 539 651 discloses a dentifrice (toothpaste or powder) which contains a calcium compound, such as hydroxyapatite, and an antibacterial metal ion carried by the calcium compound. Preferred metals are silver, zinc and copper.

KR 2004/0081936 relates to a toothpaste composition containing 0.01 to 5% by weight of cetylpyridinium chloride based on the total weight of the composition, in which the cetylpyridinium chloride is coated on the surface of granules selected from the group consisting of precipitated calcium carbonate, silica, zeolite, colloidal silica dioxide and anhydrous calcium phosphate. The coating was obtained using a fluidized-bed granulator or using an immersion method.

Carlos A. Soriano deSouza et al., in Colloids Surf. B, 87(2), 310-318 (2011), evaluated the adsorption of chlorhexidine on synthetic hydroxyapatite (HA) and its antimicrobial activity.

They demonstrated that binding chlorhexidine to HA did not affect its antimicrobial activity on *Enterococcus faecalis* growth and reduces bacterial adhesion.

EP 3 484 435 relates to an oral care composition comprising composite particles, said particles containing:

- a water-insoluble inorganic component having the formula $Ca_n(X)_x(AO_y)_z$, wherein: X is selected from OH, F and Cl; A is selected from C, P, Si and combinations thereof;

$$n = 1 \text{ to } 5;\ x = o \text{ or } 1;\ y = 3 \text{ or } 4;\ z = 1 \text{ to } 3;$$

and a cationic germicide, wherein said particles are flaky shaped, having a thickness of 15 to 80 nm. Hydroxyapatite is the preferred water-insoluble inorganic component and chlorhexidine and cetylpyridinium chloride are the preferred cationic germicides.

Okada M. et al. (Dent. Mater. J. 35(4), 651-658 (2016)) evaluated the adsorption/desorption behaviors of cetylpyridinium chloride (CPC) on HAp nanoparticles with various morphologies (spherical, short-rod, long-rod and fiber morphologies), in order to develop nanoparticulate enamel repair agents with antibacterial properties.

However, there still exists in the art the need to provide carriers, able to release the germicidal substance gradually and in response to specific conditions, which could guarantee a constant and controlled antiseptic action overtime and therefore a long-lasting protective activity.

We have surprisingly found that carbonate-hydroxyapatites (C-HAp) functionalized with specific germicides shows advantageous characteristics in the kinetics of release of incorporated germicide: when the germicide is incorporated after the formation of C-Hap particles, its release is slower and more controlled, while the germicide is incorporated during formation of C-Hap particles is more readily released in response to pH modifications. Consequently, depending on the application and the kinetics of release required, it is possible to select the more suitable synthesis for the substituted C-Hap, thus obtaining a product with slow or rapid release respectively.

Moreover, the functionalized C-Hap of the invention, compared to not-functionalized hydroxyapatite, show a more homogeneous organization of particles to form globular microaggregates. Especially for oral care application, a material with a homogeneous surface is preferred, because it improves biocompatibility, contact and substances exchange with the native tissues, thus increasing the remineralizing activity.

In addition, the calcium ions can be partially substituted by other metal cations, such as zinc, copper, and silver, increasing the release of the germicidal substances and the antibacterial activity of the functionalized C-Hap of the invention.

Carbonate-hydroxyapatite is a hydroxyapatite, wherein hydroxyl or phosphate anions are substituted by carbonate anions. Carbonate-hydroxyapatite can be successfully synthesized by carefully selecting the operating conditions (temperature, concentration, etc.) and reagents. Synthesized C-HAp mimics for composition, structure, dimensions and morphology bone apatite crystals more closely than pure synthetic Hap, and for these reasons it is also defined "biomimetic" hydroxyapatite.

As far as the Applicant knows, no one has previously described the functionalized C-Hap of the present disclosure and their advantageous properties In the present invention, the definition "carbonate-hydroxyapatite functionalized with a germicide" means that the germicide is "adsorbed on" the C-HAp or (partially) "incorporated in" the structure of the C-HAp depending on the production process.

DESCRIPTION OF THE INVENTION

It is therefore an object of the present invention a carbonate-hydroxyapatite (C-Hap), containing from 0.3 to 20% by weight (wt %) of carbonate, functionalized with from 0.01 to 10 wt % of a germicide, based on the total weight of the functionalized C-Hap, wherein said germicide is chosen among chlorhexidine and its salts, benzalkonium halides, diisobutylphenoxyethoxyethyl dimethyl benzyl ammonium halides, alkyl dimethyl ethylbenzyl ammonium halides, cetylpyridinium halides and mixtures thereof.

Cosmetic compositions comprising from 0.05 to 35 wt % of said functionalized C-HaP are another object of the invention.

It is a further object of the invention a method for the preparation of said functionalized carbonate-hydroxyapatite, the method comprising the steps of:

i) providing an aqueous solution or suspension comprising a Ca cation source and, optionally, a source of calcium-substituting metal cations;
ii) mixing the aqueous solution or suspension of step i. with an aqueous solution or suspension comprising a phosphate source;
iii) stirring the mixture so obtained in the presence of carbon dioxide or carbonate to allow the formation of a suspension of C-HAp particles wherein a germicide, chosen among chlorhexidine and its salts, benzalkonium halides, diisobutylphenoxyethoxyethyl dimethyl benzyl ammonium halides, alkyl dimethyl ethylbenzyl ammonium halides, cetylpyridinium halides, and mixtures thereof, is added to the solutions/suspension of the steps i.-iii. or is adsorbed on previously prepared C-Hap particles.

BRIEF DESCRIPTION OF THE DRAWINGS

FIG. 1. X-ray diffraction spectrum of the functionalized C-HAP of Example 1

FIG. 2. SEM image of a C-Hap.

FIG. 3. SEM image of the functionalized C-Hap of Example 1.

DETAILED DESCRIPTION OF THE INVENTION

Preferably, the functionalized carbonate-hydroxyapatite of the invention is functionalized with from 0.05 to 5 wt %, based on the total weight of the functionalized C-Hap, of said germicide.

The content of carbonate in the functionalized C-HAP according to the invention can range from 0.3 to 20 wt %, preferably from 1.0 to 12 wt %, the based on the total weight of the functionalized C-HAp. The carbonate anion can occupy two different sites in the C-HAp structure: namely, it can partially substitute the $OH^-$ anion (site A) and/or the phosphate anion (site B). According to the present invention, the carbonate ion is preferably at site B.

The carbonate-hydroxyapatite of the invention can be represented with the following formula I:

$$Ca_{(10-x)}M_x(PO_4)_{(6-2/3y)}(CO_3)_y(OH)_2 \quad \text{I}$$

where:

M is a metal cation, chosen in the group consisting of Cu, Mg, Al, Zn, Co, Fe, Ag, Mn, Sr and Ti cations or combinations of such cations;

x is comprised between 0 and 2.5, preferably between 0.05 and 2.5, more preferably between 0.1 and 2;

y is comprised between 0.1 and 3, preferably between 0.2 and 1.5.

In a preferred embodiment of the invention, in Formula I x is zero and carbonated hydroxyapatite does not contain calcium-substituting metal cations. This carbonate-hydroxyapatite can be represented by the following formula II:

$$Ca_{10}(PO_4)_{(6-2/3y)}(CO_3)_y(OH)_2 \quad \text{II}$$

wherein y can have the same values described above.

In another preferred embodiment, in Formula I x is comprised between 0.05 and 2.5, more preferably between 0.1 and 2.

Various metal cations with antibacterial activity can be incorporated into the C-HAp structure partially substituting calcium cations. Examples of these metal cations are Copper ($Cu^{2+}$), Aluminium ($Al^{3+}$), Magnesium ($Mg^{2+}$), Zinc ($Zn^{2+}$), Cobalt ($Co^{2+}$), Iron ($Fe^{3+}$ and $Fe^{2+}$), Silver ($Ag^+$), Manganese ($Mn^{2+}$), Strontium ($Sr^{2+}$), Titanium ($Ti^{4+}$) or combinations thereof.

According to a preferred embodiment of the invention, the metal-substituted C-HAp contains a cation selected among Cu, Zn, Ag cations and combinations of these cations.

According to a more preferred embodiment, the metal-substituted C-HAp contains Zn or Cu cations or combinations thereof.

The most preferred metal-substituted C-HAp contains Cu cations.

Preferably, the germicide is chosen among chlorhexidine and its salts, benzalkonium halides, cetylpyridinium halides and mixtures thereof.

More preferably, the germicide is a cetylpyridinium halide.

Cetylpyridinium chloride (CPC) is the preferred cetylpyridinium halide.

According to a preferred embodiment of the invention, the functionalized C-HAP has a crystallinity degree comprised between 15 and 85%, preferably between 15 and 70%.

The cristallinity degree can be calculated according to the following equation:

$$\%\ \text{Crystallinity}=100\cdot(C/(A+C))$$

where C and A are, respectively, the sum of the sharp peak area and the sum of the amorphous peak area (which is the area between the sharp peaks and the background in the X-ray diffraction spectrum, see FIG. 1).

Preferably, the functionalized C-HAp of the invention is in the form of particles smaller than 5 μm, preferably sized between 0.01 and 0.5 μm. Usually, the C-HAp particles are joined together to form aggregates of particles (clusters). The aggregates can have micrometric dimensions, with a size comprised between 0.1 and 50 μm, more particularly between 0.5 and 25 μm The functionalized carbonate-hydroxyapatite of the invention can be prepared by adding the germicide as reagent in the process for preparation of C-Hap particles or by adsorbing the germicide on previously prepared C-Hap particles.

The processes for the preparation of carbonate-hydroxyapatite are well known in the art. Usually, C-HAp is obtained by contacting a source of calcium cations with a source of phosphate anions, in the presence of carbon dioxide or sources of carbonate anions.

According to an embodiment of the invention, the process for the preparation of the functionalized carbonate-hydroxyapatite of the invention comprises the steps of:

i) providing an aqueous solution or suspension comprising a Ca cation source and, optionally, a source of calcium-substituting metal cations;
ii) mixing the aqueous solution or suspension of step i) with an aqueous solution or suspension comprising a phosphate source;

iii) stirring the mixture in the presence of carbon dioxide or carbonate, to allow the formation of a suspension of C-HAp particles;

wherein a germicide, chosen among chlorhexidine and its salts, benzalkonium halides, diisobutylphenoxyethoxyethyl dimethyl benzyl ammonium halides, alkyl dimethyl ethylbenzyl ammonium halides, cetylpyridinium halides, and mixtures thereof, is added to the solutions/suspension of the steps i)-iii).

Suitable sources of calcium cations are calcium fluoride, calcium chloride, calcium nitrate, calcium carbonate, calcium hydroxide, calcium acetate, or combinations thereof.

Preferably, the source of calcium cations is calcium hydroxide or calcium chloride. More preferably the source of calcium cations is calcium hydroxide.

In the process for preparing the functionalized C-HAP, the concentration of calcium cations in the aqueous solution or suspension of step i) may be from 0.15 to 10 mol/l, preferably from 0.5 to 5 mol/l.

According to a preferred embodiment of the process of the invention, the aqueous solution or suspension of step i) may further comprise a source of metal cations chosen among Cu, Mg, Al, Zn, Co, Fe, Ag, Mn, Sr and Ti cations or combinations of these cations. Suitable sources are oxides or salts of these cations or mixtures thereof.

Suitable sources of zinc cations are zinc acetate, zinc nitrate, zinc citrate, zinc fluoride, zinc chloride, zinc hydroxide, zinc carbonate or combinations thereof. Preferably, the source of zinc cations is zinc carbonate.

In the process for preparing the functionalized Zn-substituted C-HAP, the concentration of zinc cations can be from 0.01 to 5 mol/l, preferably from 0.1 to 1.5 mol/l.

Suitable sources of copper cations are copper acetate, copper nitrate, copper citrate, copper sulfate, copper chloride, copper hydroxide, copper carbonate or combinations thereof. The preferred copper cation source is copper chloride.

In the process for preparing the functionalized Cu-substituted C-HAP, the concentration of copper cations can be from 0.01 to 5 mol/l, preferably from 0.1 to 1.5 mol/l.

Suitable sources of silver cations are silver oxide, silver nitrate, silver acetate, silver sulfate, silver benzoate, silver salicylate, silver carbonate, silver citrate or silver phosphate.

In the process for preparing the functionalized Ag-substituted C-HAP, the concentration of silver cations can be from 0.01 to 5 mol/l, preferably from 0.1 to 1.5 mol/l.

Suitable sources of aluminium cations are aluminium chloride, aluminium hydrochloride, aluminium sulphate, aluminium nitrate or mixtures thereof. Preferably, the source of aluminium cations is aluminium chloride.

In the aqueous solution or suspension of step i), the aluminium cations can be present at a concentration of from 0.02 to 5.0 mol/l, preferably from 0.1 to 3.0 mol/l.

Suitable sources of magnesium cations are magnesium hydrogen phosphate, trimagnesium phosphate, magnesium dihydrogen phosphate, magnesium chloride, magnesium chloride hexahydrate, magnesium glycerophosphate, magnesium hydroxide, magnesium hydroxide carbonate, magnesium oxide, magnesium citrate, magnesium silicate or mixtures thereof. Preferably, the source of magnesium cations is magnesium chloride hexahydrate.

In the process for preparing the functionalized Mg-substituted C-HAp, the magnesium cation can be used at an initial concentration from 0.005 to 3.0 mol/l, preferably from 0.05 to 1.0 mol/l.

Preferably, the aqueous solution or suspension of step i) has a pH comprised between 7 and 13, more preferably between 8 and 12.

Suitable sources of phosphate anions are disodium hydrogen phosphate, sodium dihydrogen phosphate, orthophosphoric acid, dipotassium hydrogen phosphate, potassium dihydrogen phosphate, di-ammonium hydrogen phosphate or combinations thereof. Preferably, the source of phosphate anions is orthophosphoric acid.

In the process for preparing the functionalized C-HAp, the concentration of the phosphate anions in the aqueous solution or suspension of step ii) can range from 0.05 to 10 mol/l, preferably from 0.5 to 5 mol/l.

Step ii) can be carried out over a time comprised between 30 minutes and 2 hours at a temperature below 60° C., preferably from 30 to 50° C.

In the process of the invention, step iii) allow the development of the particles of functionalized carbonate-hydroxyapatite to the desired size and structure. Usually, step iii) is carried out for at least 6 hours at a temperature below 60° C. Preferably, step iii) is carried out for 6 to 36 hours and more preferably for 12 to 24 hours at a temperature comprised between 25 and 45° C.

The carbonate substitution of phosphate may be advantageously achieved out by simply agitating the solution or suspension for example by means of a mechanical stirrer in the presence of a carbon dioxide gas or may be achieved by bubbling a carbon dioxide gas into the liquid phase or by combining a mechanical stirring with a gas bubbling.

The carbon dioxide gas may be a gas containing carbon dioxide. Pure carbon dioxide gas or air may be used as the carbon dioxide gas.

Alternatively, a carbonate salt may be added in advance to the aqueous solution or suspension of step i) or to the solution or suspension comprising the phosphate source. Otherwise, a carbonate salt may be added to the mixture obtained in step ii).

Further, step ii) may be carried out by simultaneously adding a solution or suspension containing the carbonate salt and another solution or suspension containing phosphate anions to the aqueous solution or suspension of step i).

Ammonium carbonate, sodium bicarbonate, sodium carbonate, potassium carbonate, or potassium bicarbonate may be used as the carbonate salt. Alternatively, in the case of a metal-substituted C-Hap, the carbonate source can be a carbonate salt of the substituting metal.

The concentration of the carbonate salt can range, for example, from 0.01 to 3.0 mol/l.

Similarly, the germicide can be added to the solutions or suspensions of steps i) and ii) or to the mixture of step iii), or can be added as an independent solution in step ii). Preferably, the germicide is added to the mixture at the beginning of step iii).

The concentration of the germicide can range, for example, from 0.001 to 1.0 mol/l.

In an embodiment of the invention, the process for the preparation of the functionalized C-Hap further comprises the following steps:

iv) separating the functionalized carbonate-hydroxyapatite particles from the suspension obtained from step iii);

v) and drying the wet particles.

The separation of step iv) is carried out using techniques well known to the person skilled in the art, for example by decantation, centrifugation, filtration, spray-drying and the like.

In step v), the powder is dried, for instance by freeze-drying or drying in a ventilated or a vacuum oven at 40-90° C., and reduced to the granulometry suitable for the desired uses.

In a preferred embodiment, the process may also comprise an additional step of washing the separated particles with water or a basic solution prior to the drying step v). The washing operation can be repeated several times, if desired. Advantageously, the optional washing step is useful for removing any reagent residues possibly adsorbed or trapped by the particles aggregates.

In a further embodiment, the functionalized C-HAp of the invention can be prepared by functionalizing C-Hap particles, optionally metal-substituted, prepared according to the above described process, but without any addition of germicide. These C-Hap particles can be functionalized by adsorption from a concentrated solution of the germicide, as described, for example, in Okada M. et al., Dent. Mater. J. 35(4), 651-658 (2016).

The C-HAp functionalized with a germicide of the invention can be used for the preparation of cosmetic compositions comprising from 0.05 to 35 wt %, preferably from 0.5 to 25 wt %, of said functionalized carbonate-hydroxyapatite.

Preferred cosmetic compositions are oral care compositions or skin-care compositions.

Examples of skin-care compositions are hand-sanitizers, lotions for feet, deodorants, lipsticks, and the like.

Examples of oral care compositions are toothpastes, tooth powders, chewing gums for oral and dental hygiene, mouthwashes and mouth bath concentrates and gargles.

EXAMPLES

Example 1

45 ml of deionized water containing 0.013 moles of $H_3PO_4$ and 0.0022 moles of cetylpyridinium chloride monohydrate were added dropwise under stirring to a 50 ml of deionized water containing 0.2 moles of $Ca(OH)_2$ and 0.015 moles of $CaCO_3$ at a temperature of 37° C. The phosphoric acid solution was added over a time of about 60 min. The suspension so obtained was maintained at a temperature of 37° C. for 24 hours under stirring.

The functionalized C-Hap particles were recovered by centrifugation (at 6000 revolutions per minute for 20 minutes) and were washed three times with deionized water.

At the end of the preparation, the functionalized C-Hap particles were dried in oven under vacuum at 80° C.

Example 2

30 ml of deionized water containing 0.013 moles of $H_3PO_4$ in were added dropwise under stirring to 50 ml of deionized water containing 0.2 moles of $Ca(OH)_2$ and 0.015 moles of $CaCO_3$ in at a temperature of 37° C. The phosphoric acid solution was added over a time of about 60 min.

At the end of the addition, 15 ml of deionized water containing 0.0022 moles of cetylpyridinium chloride monohydrate were added dropwise to the reaction mass under stirring.

The suspension so obtained was maintained at a temperature of 37° C. for 24 hours under gentle stirring.

The functionalized C-Hap particles were recovered by centrifugation (at 6000 rpm for 20 minutes) and were washed three times with deionized water.

At the end of the preparation, the functionalized C-Hap particles were dried in oven under vacuum at 80° C.

Example 3

30 ml of deionized water containing 0.013 moles of $H_3PO_4$ in were added dropwise under stirring to 50 ml of deionized water containing 0.18 moles of $Ca(OH)_2$, 0.02 moles of Copper Sulfate and 0.02 moles of $Na_2CO_3$ at a temperature of 37° C. The phosphoric acid solution was added over a time of about 60 min.

Preparation continues with 15 ml of deionized water containing 0.0022 moles of cetylpyridinium chloride monohydrate were added dropwise to the reaction mass under stirring.

The suspension so obtained was maintained at a temperature of 37° C. for 24 hours under gentle stirring.

The functionalized Cu substituted C-Hap particles were recovered by centrifugation (at 6000 rpm for 20 minutes) and were washed three times with deionized water.

At the end of the preparation, the functionalized Cu substituted C-Hap particles were dried in oven under vacuum at 80° C.

Table 1 reports the amount CPC in the functionalized C-HAp of Examples 1-3.

TABLE 1

| | CPC % |
|---|---|
| Example 1 | 0.6 |
| Example 2 | 0.6 |
| Example 3 | 0.6 |

The concentration of CPC in the functionalized C-Hap was determined by UV-Vis Spectrophotometric Analysis, according to the European Pharmacopoeia.

Briefly, 1 mg of functionalized C-Hap was solubilized in 1 ml of HCl 0.1 M and the amount of CPC in the solution was determined by reading the absorbance at 259 nm.

X-Ray Diffraction Characterization

The C-HAP functionalized with CPC of Example 1 was dried and characterized with a MiniFlex X-ray diffractometer (Rigaku), with the following settings:

Voltage: 30 kV
Current: 15 mA
Radiation Type: Cu
Radiation Wavelength: 1.54056 Å
2θ range: 10° to 60° with step of 0.02°
Scan speed: 2° (2θ)/min The diffraction spectrum (FIG. 1) shows the typical peaks of a hydroxyapatite as reported in literature (standard hydroxyapatite deposited in the ICDD Diffraction data Database. File n. 01-086-1199). However, the sample results poorly crystalline; the large diffraction (diffusion) peaks detected are due to a low degree of crystallinity, induced by the conditions of synthesis.

The cristallinity degree for the functionalized C-HAP of Example 1 is 30±5%.

Scanning Electron Microscopy Characterization

Functionalized C-Hap was further characterized by Scanning Electron Microscopy (SEM).

SEM imaging highlighted that, compared to a carbonate-hydroxyapatite (FIG. 2), the CPC functionalized C-Hap of Example 1 (FIG. 3) shows a more homogeneous organization of particles to form globular microaggregates in suspension.

This behaviour allows to create a regular exchange surface of the composite that, together with lower crystallinity and the higher reactivity, is responsible for the controlled release of the cetylpyridinium chloride.

Release of Cetylpyridinium Chloride

The release over the time of the CPC from the functionalized C-Hap was evaluated by putting 150 mg of functionalized C-Hap particles in 5 ml of two buffers at different pH. The variation in the CPC concentration in the buffer solutions was determined by UV-Vis spectrophotometry.

The results are reported in Table 2.

TABLE 2

| Release % | pH | 30 min | 1.0 h | 2.0 h | 5.0 h |
|---|---|---|---|---|---|
| Example 1 | 5.5 | 78 | 84 | 87 | 89 |
| | 6.3 | 55 | 77 | 86 | 90 |
| Example 2 | 5.5 | 62 | 70 | 72 | 73 |
| | 6.3 | 36 | 50 | 60 | 68 |

The results summarized in Table 2 show the functionalized C-Hap obtained according to Example 1 and Example 2 release CPC overtime in a pH dependent manner.

Indeed, lower pH (from 6.3 to 5.5) promotes the release of CPC from C-Hap, thus inducing a more rapid achievement of active concentrations of cetylpyridinium chloride (already after 30 minutes) in the site of application.

When used in cosmetic products for skin- and personal care such as deodorants, hand sanitizers, feet lotions, lipsticks etc., due to the pH of skin (around 5.5), functionalized C-Hap can release CPC more rapidly, thus allowing an effective, but still long-lasting, protection of the skin against microorganisms.

When applied on areas with higher pH, for example in the mouth through oral care products, the CPC will be slowly released. The functionalized C-Hap will have the time to get fixed on the enamel surface preventing the formation of the biofilm that constitutes the plaque. The postprandial lowering of pH of the oral mucosa (due to the consumption of food), will allow to increase the release of CPC, advantageously reducing the microbial population responsible for plaque formation.

The invention claimed is:

1. A functionalized carbonate-hydroxyapatite containing from 0.3 to 20% by weight (wt %) of carbonate, wherein the functionalized carbonate-hydroxyapatite is in the form of globular microaggregates, and wherein the functionalized carbonate-hydroxyapatite is functionalized with from 0.01 to 10 wt % of a germicide, based on the total weight of the functionalized carbonate-hydroxyapatite, wherein said germicide is selected from the group consisting of chlorhexidine and its salts, benzalkonium halides, diisobutylphenoxyethoxyethyl dimethyl benzyl ammonium halides, alkyl dimethyl ethylbenzyl ammonium halides, cetylpyridinium halides, and mixtures thereof;

wherein the functionalized carbonate-hydroxyapatite is represented by Formula I:

$$Ca_{(10-x)}M_x(PO_4)_{(6-2/3y)}(CO_3)_y(OH)_2 \quad \text{I}$$

where:

M is a metal cation selected from the group consisting of Cu, Mg, Al, Zn, Co, Fe, Ag, Mn, Ti, and any combination thereof;

x is between 0 and 2.5; and y is between 0.1 and 3.

2. The functionalized carbonate-hydroxyapatite of claim 1, functionalized with from 0.05 to 5 wt % of the germicide, based on the total weight of the functionalized carbonate-hydroxyapatite.

3. The functionalized carbonate-hydroxyapatite of claim 1, wherein said germicide is a cetylpyridinium halide.

4. The functionalized carbonate-hydroxyapatite of claim 1, wherein in Formula I x is zero.

5. The functionalized carbonate-hydroxyapatite of claim 1, wherein in Formula I, x is between 0.1 and 2.

6. The functionalized carbonate-hydroxyapatite of claim 1, wherein M is Cu, Zn, Ag, or any combination thereof.

7. A cosmetic composition, comprising from 0.05 to 35 wt % of a functionalized carbonate-hydroxyapatite containing from 0.5 to 20 wt % of carbonate, wherein the functionalized carbonate-hydroxyapatite is in the form of globular microaggregates, and wherein the functionalized carbonate-hydroxyapatite is functionalized with from 0.01 to 10 wt % of a germicide, based on the total weight of the functionalized carbonate-hydroxyapatite, wherein said germicide is selected from the group consisting of chlorhexidine and its salts, benzalkonium halides, diisobutylphenoxyethoxyethyl dimethyl benzyl ammonium halides, alkyl dimethyl ethylbenzyl ammonium halides, cetylpyridinium halides and mixtures thereof.

8. The cosmetic composition of claim 7, comprising from 0.5 to 25 wt % of said functionalized carbonate-hydroxyapatite.

9. The cosmetic composition of claim 7, wherein said cosmetic composition is an oral care composition or a skin-care composition.

10. The cosmetic composition of claim 7, wherein the functionalized carbonate-hydroxyapatite is represented by Formula I:

$$Ca_{(10-x)}M_x(PO_4)_{(6-2/3y)}(CO_3)_y(OH)_2 \quad \text{I}$$

where:

M is a metal cation selected from the group consisting of Cu, Mg, Al, Zn, Co, Fe, Ag, Mn, Ti, and any combination thereof;

x is between 0 and 2.5; and y is between 0.1 and 3.

11. The cosmetic composition of claim 10, wherein M is Cu, Zn, Ag, or any combination thereof.

12. The functionalized carbonate-hydroxyapatite of claim 1, wherein the germicide functionalizes a carbonate-hydroxyapatite during synthesis thereof.

13. The cosmetic composition of claim 7, wherein the germicide functionalizes a carbonate-hydroxyapatite during synthesis thereof.

14. The cosmetic composition of claim 7, wherein the globular microaggregates have a size ranging from about 0.1 μm to about 50 μm.

* * * * *